US005902801A

United States Patent [19]
Schleck et al.

[11] Patent Number: 5,902,801
[45] Date of Patent: May 11, 1999

[54] GLUCOSAMINE SULFATE METAL CHLORIDE COMPOSITIONS AND PROCESS OF PREPARING SAME

[75] Inventors: James R. Schleck, Somerset; Christopher M. Burger, Toms River; Vilas M. Chopdekar, Edison, all of N.J.

[73] Assignee: Jame Fine Chemicals, Inc., Bound Brook, N.J.

[21] Appl. No.: 09/191,169

[22] Filed: Nov. 13, 1998

Related U.S. Application Data

[63] Continuation-in-part of application No. 09/083,173, May 22, 1998, Pat. No. 5,843,923.
[51] Int. Cl.$^6$ .............................. C07H 5/06; A01N 43/04
[52] U.S. Cl. ..................... 514/62; 536/18.7; 536/55.2; 536/55.3; 536/17.2; 514/23; 514/62
[58] Field of Search .................. 536/55.3, 55.2, 536/17.9, 29.1, 17.2; 514/62

[56] References Cited

U.S. PATENT DOCUMENTS 3,683,076  8/1972  Rovati ..................................... 424/180
4,642,340  2/1987  Senin et al. ............................. 535/55.2
5,663,415  9/1997  Chopdekar et al. ..................... 560/68

FOREIGN PATENT DOCUMENTS 0214642  3/1987  European Pat. Off. .......... C07H 5/06

*Primary Examiner*—James O. Wilson
*Assistant Examiner*—Howard Owens
*Attorney, Agent, or Firm*—Jack Matalon

[57] ABSTRACT

Glucosamine compositions comprising the compounds glucosamine sulfate metal chloride, wherein the metal, i.e. the cation, is lithium, sodium, magnesium, zinc or manganese. The compounds have purity levels of at least about 97%, with water present in a maximum amount of about 10 wt. %, based on the weight of the composition. The compounds are prepared by contacting glucosamine hydrochloride with the metal sulfate in the presence of water to form an aqueous solution of glucosamine sulfate metal chloride and thereafter freeze-drying the solution at a temperature and at a reduced pressure for such period of time that at least about 90 wt. % of the water is removed and decomposition of the compound glucosamine sulfate metal chloride is limited to a maximum of about 3%.

14 Claims, No Drawings

GLUCOSAMINE SULFATE METAL CHLORIDE COMPOSITIONS AND PROCESS OF PREPARING SAME

REFERENCE TO RELATED APPLICATION

This application is a continuation-in-part of our application Ser. No. 09/083,173 filed May 22, 1998, now U.S. Pat. No. 5,843,923, issued Dec. 1, 1998.

FIELD OF INVENTION

The invention relates to glucosamine sulfate metal chloride compositions and processes for preparing same. The glucosamine sulfate metal chloride compositions of the invention are true compounds having a purity level of at least about 97%.

BACKGROUND OF THE INVENTION

Glucosamine is a well known and widely used substance for the treatment of rheumatic fever, arthritic and arthosic complaints, in the acute as well as chronic forms, as well as in the treatment of pathological conditions originating from metabolic disorders of the osteo-articular tissue. Although products in the market-place are labelled as, or referred to as, "glucosamine sulfate" or "stabilized glucosamine sulfate", they are misnomers, since such products are not true compounds, but rather unreacted mixtures of glucosamine hydrochloride and a salt such as potassium or sodium sulfate.

Mixed salts of glucosamine hydrochloride and alkaline or earth alkaline metal sulfates such as potassium sulfate, and sodium sulfate are well known. Such mixed salts are used rather than glucosamine sulfate alone since the latter is unstable in view of its highly hygroscopic nature and the facility with which its amino group oxidizes if not completely saltified, see e.g. U.S. Pat. No. 4,642,340 and U.S. Pat. No. 3,683,076 which discloses a mixture of glucosamine sulfate and glucosamine hydroiodide.

Free glucosamine base may be prepared by the method recited in *Chem. Ber.*, volume 75, page 1274. Such method involves the treatment of glucosamine hydrochloride with an ethanolic solution of a tertiary base such as triethylamine. Triethylamine hydrochloride is filtered off and the free glucosamine is then recovered from the reaction mixture. However, triethylamine is a toxic material even in small quantities and the yield of the free glucosamine base is quite low.

In EP 0 214 642, free glucosamine base is converted to a mixed salt of glucosamine sulfate and potassium chloride by dissolving the glucosamine base in water, adding a stoichiometric quantity of concentrated sulfuric acid to form a solution of glucosamine sulfate in water and dissolving a stoichiometric amount of potassium chloride in the solution. The mixed salt is precipitated from the solution by addition of a precipitant such as isopropanol, stirring the mixture for about 14 hours to complete the precipitation, cooling the reaction mass to 0° C. and recovering the precipitated salt by filtration. This process results in low yields.

SUMMARY OF THE INVENTION

It has now been found possible to prepare compositions comprising true compounds of glucosamine sulfate metal chlorides, wherein the metal, i.e. the cation, is lithium, sodium, magnesium, zinc or manganese. The compounds will have a purity level of about 97%, preferably at least 99%. Moreover, the processes of the invention avoids the use of toxic reagents such as triethylamine and also avoids the use of precipitants such as isopropanol, thereby permitting substantially quantitative yields with little or no impurities present other than very minor quantities of water.

DETAILED DESCRIPTION OF THE INVENTION

The invention pertains to novel compositions and processes for preparing same. The compositions comprise:

(a) glucosamine sulfate metal chloride compounds having a purity level of at least about 97%, wherein the metal, i.e. the cation, is selected from the group consisting of lithium, sodium, magnesium, zinc and manganese; and (b) water, present in a maximum amount of about 10 wt.%, based on the weight of the composition.

Preferably, the compounds will have purity levels of at least 99%. Indeed, the processes of the invention typically result in compounds having purity levels in excess of 99%. The principal impurity will be water which is preferably present in a maximum amount of 5 wt. %, based on the weight of the composition. Typically, the processes of the invention will produce compositions with water contents of not greater than 3 wt. %.

Any water present in the compositions of the invention is not to be regarded as an "impurity" in the classical sense. The compositions of the invention are intended to be ingested and minor adjustments in the dosage to be ingested can be readily made to account for such water.

Prior art compositions referred to as glucosamine sulfate potassium chloride or glucosamine sulfate prepared using isopropanol or acetone as a precipitant exhibit unacceptable chloride assay values of about 93% and densities of 0.55–0.65, indicating that potassium chloride is abstracted from the composition and remains in the aqueous precipitant layer.

The glucosamine sulfate metal chloride compounds of the invention have densities which vary depending on the particular metal chloride, and are set forth in the Examples below. The chloride assay value of the compounds of the invention remain about 100 wt. %, prior to and subsequent to nitrogen sparging, which indicates that true compounds, rather than mixtures of salts or mixtures of reacted components plus unreacted components have been prepared by the processes of the invention. Also as discussed below, a simple test involving the addition of the composition to a mixture of liquid halogenated aliphatic hydrocarbons with a density of about 2.0 g/cc will readily verify whether a composition alleged to be stabilized glucosamine sulfate, i.e. glucosamine sulfate metal chloride is a true compound or is a mixture of unreacted glucosamine hydrochloride and a metal sulfate. In the presence of the halogenated hydrocarbons, the true compound will float as a layer on the top, whereas some of the mixture of unreacted glucosamine hydrochloride and the metal sulfate will float on the top and some of such mixture will fall as a precipitate to the bottom.

The processes for preparing the novel compositions of the invention are quite simple and straightforward and typically result in quantitative yields. The processes involves the following steps:

(a) contacting glucosamine hydrochloride with a metal sulfate in the presence of water to form an aqueous solution of glucosamine sulfate metal chloride, wherein the metal is lithium, sodium, magnesium, zinc or manganese; and (b) recovering the compound glucosamine sulfate metal chloride by freeze-drying the solution from step (a) at a temperature and at a reduced pressure for such period of time that: (i) at least about 90 wt. % of the water is removed and (ii) decomposition of the compound is limited to a maximum of about 3 wt. %.

Typically, the glucosamine hydrochloride and metal sulfate are contacted in stoichiometric quantities in the presence of sufficient water to form a concentration of solids of about 15 to 40 wt. %, preferably 20 to 30 wt. %, and the contacting, i.e. step (a) takes place for a period of about 15 minutes to 2 hours. Step (a) takes place at temperatures, of about 20 to about 45° C. Higher temperatures are undesirable since exposure to such higher temperatures for prolonged periods of time will lead to decomposition, as evidenced by a yellowing of the solution.

The freeze-drying in step (b) is typically carried out at a pressure of not greater than about 800 milliTorr, preferably 300 to 500 milliTorr, and at a temperature in the range of about −60° C. to 0° C., preferably −40 to −5° C.

The processes of the invention avoid the use of precipitants such as isopropanol, acetone, dioxane, etc. in order to recover the glucosamine sulfate metal chloride from the aqueous reaction mixture.

It has also been found that if removal of the water by distillation is used to recover the glucosamine sulfate metal chloride, some decomposition of the product occurs, even if the distillation is carried out at moderate temperatures of about 50° C. and at a pressure of about 20 mm Hg. Decomposition of the product is evidenced by a yellowing of the product and a shift in taste from sweetish and slightly salty to a bitter taste. When the water is attempted to be removed under vacuum at a pressure of about 20 mm Hg at ambient temperatures, significant foaming of the reaction mass occurs which prevents the water from being distilled off without also causing the product to flow out of the flask containing the aqueous solution.

The following non-limiting examples shall serve to illustrate the various embodiments of this invention. Unless otherwise indicated to the contrary, all parts and percentages are on a weight basis.

EXAMPLE 1

Glucosamine sulfate sodium chloride was prepared by the following procedure. A one-liter, three-necked flask equipped with a thermometer, stirrer, heating mantle and condenser was charged with 1720 g of purified water and 431.5 g (2.0 moles) of glucosamine hydrochloride. The glucosamine hydrochloride promptly went into solution, with stirring (the dissolution of the glucosamine hydrochloride was endothermic in nature). After stirring for a few minutes, 142 g (1.0 mole) of sodium sulfate was added to the solution and stirring was continued for about one hour at 35–40° C. to complete the reaction.

The water was then stripped off from the resultant clear solution of by freeze-drying under the following conditions:

The freeze temperature was set at −40° C., the condenser set point was −45° C., the vacuum set point was 200.0 milliTorr and the vacuum safety was set at 800 milliTorr. The solution was then subjected to the following freeze-drying steps:

| Step | Temp. ° C. | Time, minutes |
|---|---|---|
| 1 | −30 | 120 |
| 2 | −15 | 300 |

| Step | Temp. ° C. | Time, minutes |
|---|---|---|
| 3 | −5 | 540 |
| 4 | 0 | 540 |
| 5 | 10 | 300 |
| 6 | 20 | 240 |
| Post Heat | 25 | 60 |

After freeze drying, glucosamine sulfate sodium chloride was obtained as a white powder in a yield of 556 g (97% of theoretical).

EXAMPLE 2

Example 1 was repeated using 1655 g of purified water, 431.5 g (2 moles) of glucosamine hydrochloride and 120.3 g (1 mole) of magnesium sulfate instead of the sodium sulfate. After freeze drying, glucosamine sulfate magnesium chloride was obtained as a white powder in a yield of 530 g (96% of theoretical).

EXAMPLE 3

Example 1 was repeated using 1855 g of purified water, 431.5 g (2 moles) of glucosamine hydrochloride and 287.5 g (1 mole) of zinc sulfate (heptahydrate) instead of the sodium sulfate. After freeze drying, glucosamine sulfate zinc chloride was obtained as a white powder in a yield of 540 g (95% of theoretical).

EXAMPLE 4

Example 1 was repeated using 1679 g of purified water, 431.5 g (2 moles) of glucosamine hydrochloride and 128 g (1 mole) of lithium sulfate (monohydrate) instead of the sodium sulfate. After freeze drying, glucosamine sulfate lithium chloride was obtained as a white powder in a yield of 525 g (97% of theoretical).

EXAMPLE 5

Example 1 was repeated using 450 g of purified water, 107.8 g (0.5 mole) of glucosamine hydrochloride and 42.3 g (0.25 mole) of manganese sulfate monohydrate instead of the sodium sulfate. After freeze drying, glucosamine sulfate manganese chloride was obtained as a white powder in a yield of 144 g (98% of theoretical).

EXAMPLE 6

The purpose of this example was to measure the specific rotation of mixtures of glucosamine hydrochloride and metal sulfates, as distinguished from the glucosamine sulfate metal chloride true compounds of the invention.

The mixtures were prepared by mixing glucosamine hydrochloride and the metal sulfate in a 2:1 molar ratio in sufficient purified water to yield a 20 wt. % solution (at 20° C.). The solutions were filtered through Whatman #4 filter paper and were then checked (at 20° C.) for specific rotation 10 minutes, 2 hours and 24 hours later.

The true compounds of the invention obtained by freeze drying as set forth in Examples 1–5, i.e. the glucosamine sulfate metal chlorides, were dissolved in sufficient purified water to yield 20 wt. % solutions (at 20° C.), filtered through Whatman #4 filter paper and then checked (at 20° C.) for specific rotation 10 minutes, 2 hours and 24 hours later.

As may be seen in Table 1, the specific rotations of the mixtures consistently change throughout the 24-hour period (at 20° C.) whereas the specific rotations of the true compounds of the invention obtained as set forth in Examples 1–5 remained constant, thus indicating by a simple specific rotation test whether a mixture or a true compound is present. In Table 1, a specific rotation comparison was also made between a glucosamine hydrochloride potassium sulfate mixture prepared as described above and a 20 wt. % solution of glucosamine sulfate potassium chloride prepared by the process described in Example 3 of our co-pending application Ser. No. 09/083,173 filed May 22, 1998.

chloride mixed with sodium sulfate, glucosamine hydrochloride mixed with magnesium sulfate, glucosamine hydrochloride mixed with zinc sulfate and glucosamine hydrochloride mixed with manganese sulfate as well as the compounds glucosamine sulfate.2 potassium chloride (Example 3 of Ser. No. 09/083,173), glucosamine sulfate.2 sodium chloride (Example 1 above), glucosamine sulfate-.magnesium chloride (Example 2 above), glucosamine sulfate.zinc chloride (Example 3 above) and glucosamine sulfate.manganese chloride (Example 5 above). A second

TABLE 1

| Product | Method of Preparation | Spec. Rot. 10 minutes | Spec. Rot. 2 hours | Spec. Rot. 24 hours |
|---|---|---|---|---|
| GHCl + $K_2SO_4$ | Synthetic Mixture | 80 | 68 | 52 |
| GS.2KCl | Ex. 3 of SN 09/083,173 | 51.8 | 51.8 | 51.8 |
| GHCl + $Na_2SO_4$ | Synthetic Mixture | 80 | 70 | 55 |
| GS.2NaCl | Example 1 above | 56 | 55 | 55 |
| GHCl + $Li_2SO_4$ | Synthetic Mixture | 80 | 68 | 58 |
| GS.2LiCl | Example 4 above | 58.5 | 57.5 | 57.5 |
| GHCl + $MgSO_4$ | Synthetic Mixture | 80 | 70 | 56 |
| $GS.MgCl_2$ | Example 2 above | 57 | 56.3 | 56.3 |
| GHCl + $ZnSO_4$ | Synthetic Mixture | 80 | 68 | 53.8 |
| $GS.ZnCl_2$ | Example 3 above | 53.8 | 52.5 | 52.5 |
| GHCl + $MnSO_4$ | Synthetic Mixture | 78 | 66 | 55 |
| $GS.MnCl_2$ | Example 5 above | 54.6 | 54.6 | 54.6 |

GHCl = glucosamine hydrochloride; GS = glucosamine sulfate

EXAMPLE 7

The purpose of this example was to measure the tap densities of synthetic mixtures of glucosamine hydrochloride and metal sulfates and the freeze-dried compounds of the invention. The results are set forth in Table 2.

TABLE 2

| Product | Source | Density, g/cc |
|---|---|---|
| GHCl + $K_2SO_4$ | Synthetic mixture | 1.2 |
| GS.2KCl | Ex. 3 of SN 09/083,173 | 0.92 |
| GHCl + $Na_2SO_4$ | Synthetic mixture | 1.14 |
| GS.2NaCl | Example 1 above | 0.55 |
| GHCl + $MgSO_4$ | Synthetic mixture | 1.09 |
| $GS.MgCl_2$ | Example 2 above | 0.65 |
| GHCl + $ZnSO_4$ | Synthetic mixture | 1.16 |
| $GS.ZnCl_2$ | Example 3 above | 0.95 |
| GHCl + $Li^2SO_4$ | Synthetic mixture | 1.00 |
| GS.2LiCl | Example 4 above | 0.8 |
| GHCl + $MnSO_4$ | Synthetic Mixture | 1.19 |
| $GS.MnCl_2$ | Example 5 above | 0.93 |

EXAMPLE 8

Dibromomethane, 58 cc (144 g), density of 2.48 g/cc, was mixed with dichloromethane, 42 cc (56 g), density 1.3 g/cc to yield 100 cc of a first solvent having a density of 2.0 g/cc. The first solvent was used to evaluate glucosamine hydrochloride mixed with potassium sulfate, glucosamine hydrosolvent was prepared by mixing dibromomethane, 35 cc (87 g), density of 2.48 g/cc with 65 g dichloromethane, 65 cc (85 g), density of 1.3 g/cc to yield 100 cc of a second solvent having a density of 1.7 g/cc. The second solvent was used to evaluate glucosamine hydrochloride mixed with lithium sulfate and the compound glucosamine sulfate 2 lithium chloride (Example 4 above).

The evaluations of the mixtures and compounds were carried out by placing 2 g of the mixture or compound in a vial together with 10 cc of the first or second solvent and shaking the vial for a few seconds. After allowing the vial to stand for ten minutes, it was noted that the vials containing the mixture showed a layer floating on the surface of the solvent and a precipitate, whereas in the case of the vials containing the compounds, all of the material floated on the surface of the solvent, without the appearance of any precipitate.

The mixtures and the compounds were initially assayed by titration for chloride content prior to mixing with the first or second solvent. After the ten minute period subsequent to the mixing of the mixtures and compounds with the first or second solvent, the surface layers in all of the vials, i.e. the top fractions, as well as the precipitates in all of the vials, i.e. the bottom fractions, were also assayed for % chloride content by titration and their specific rotations were also measured. The results are set forth in Table 3.

TABLE 3

| | | | Top Fraction | | Bottom Fraction | |
|---|---|---|---|---|---|---|
| Product | Source | Initial Assay | Sp. Rot. | Assay | Sp. Rot. | Assay |
| GHCl + $K_2SO_4$ | Synthetic mixture | 98.6% | 74 | 138% | 1.4 | 2.7% |
| GS.2KCl | Ex. 3 of SN 09/083,173 | 100.3% | 51.8 | 99.8% | No bottom fraction | |
| GHCl + $Na_2SO_4$ | Synthetic mixture | 101.0% | 68 | 120.1% | 2.0 | 3.6% |

TABLE 3-continued

| | | | Top Fraction | | Bottom Fraction | |
|---|---|---|---|---|---|---|
| Product | Source | Initial Assay | Sp. Rot. | Assay | Sp. Rot. | Assay |
| GS.2NaCl | Example 1 above | 99.1% | 55 | 99.3% | No bottom fraction | |
| GHCl + MgSO$_4$ | Synthetic mixture | 99.6% | 69 | 123.1% | 9.0 | 14.1% |
| GS.MgCl$_2$ | Example 2 above | 100.0% | 56.3 | 100.2% | No bottom fraction | |
| GHCl + ZnSO$_4$ | Synthetic mixture | 100.5% | 71 | 126.2% | 2.0 | 3.6% |
| GS.ZnCl$_2$ | Example 3 above | 99.1% | 52.5 | 99.6% | No bottom fraction | |
| GHCl + Li$_2$SO$_4$ | Synthetic mixture | 98.9% | 70 | 121.0% | 11.0 | 9.3% |
| GS.2LiCl | Example 4 above | 97.0% | 58.5 | 98.3% | No bottom fraction | |
| GHCl + MnCl$_2$ | Synthetic mixture | 98.9 | 68 | 124.2% | 12.0 | 9.6% |
| GS.MnCl$_2$ | Example 5 above | 98.8 | 55 | 99.1% | No bottom fraction | |

EXAMPLE 9

In this example, a comparison of the various materials was carried out using the following procedure: A 1-liter glass beaker was provided with a paper thimble of 12.1 cm in length and 4.4 cm in diameter. A glass tube with a fritted end having a length of 25.4 cm, an outer diameter of 7.6 mm and an inner diameter of 5.1 mm was inserted into the thimble such that the end thereof was approximately 5 mm from the bottom of the thimble. Glucosamine salts and glucosamine compounds prepared as synthetic mixtures and by the freeze drying method of the invention, respectively, in the amount of 50 g for each salt and each compound were placed in the thimble and the open end of the glass tube was connected to a nitrogen gas cylinder. Nitrogen was sparged through the frit at the rate of 56.6 liters/minute for approximately 15 minutes and lighter material cascaded over the thimble and was collected in the beaker. The material in the thimble was assayed by titration for chloride prior to commencement of nitrogen sparging (initial assay). The fraction sparged out was measured for specific rotation and also assayed by titration for % chloride. The fraction remaining in the thimble was measured for specific rotation. The results are set forth in Table 4.

TABLE 4

| | | | Top Fraction | | Bottom Fraction |
|---|---|---|---|---|---|
| Product | Source | Initial Assay | Sp. Rot. | Assay | Specific Rotation |
| GHCl + Na$_2$SO$_4$ | Synthetic mixture | 101 | 66 | 121 | 35 |
| GS.2NaCl | Example 1 above | 99.1 | 55 | 99.6 | 55 |
| GHCl + MgSO$_4$ | Synthetic mixture | 99.6 | 65.5 | 119 | 32 |
| GS.MgCl$_2$ | Example 2 above | 100 | 56 | 100.6 | 56 |
| GHCl + ZnSO$_4$ | Synthetic mixture | 100.5 | 68 | 128 | 28 |
| GS.ZnCl$_2$ | Example 3 above | 99.1 | 52.5 | 99.8 | 53 |
| GHCl + Li$_2$SO$_4$ | Synthetic mixture | 98.9 | 68 | 116 | 34 |
| GS.2LiCl | Example 4 above | 97.8 | 58.5 | 98 | 58.5 |
| GHCl + MnSO$_4$ | Synthetic mixture | 98.9 | 65 | 118.6 | 37 |
| GS.MnCl$_2$ | Example 5 above | 98.8 | 54.6 | 99.2 | 54.6 |

As may be seen from Table 4, the synthetic mixtures and the compounds of the invention, had satisfactory initial assays, before nitrogen sparging. However, after sparging, the assays obtained for the synthetic mixtures from the material sparged out of the thimble were considerably different from the initial assays indicating that such materials were mixtures and not true compounds. This was further reinforced by the different specific rotation values obtained in respect to the material sparged out versus those of the material remaining in the thimble. On the other hand, the materials prepared by the freeze drying method recited in Examples 1–5 above were clearly true compounds as evidenced by no change in the assay values prior to, and subsequent to, sparging as well as the top fraction and the remaining fraction having the same specific rotation values, after sparging.

What is claimed is:

1. A composition comprising:
   (a) the compound glucosamine sulfate metal chloride, wherein the metal is selected from the group consisting of lithium, sodium, magnesium, zinc and manganese, said compound having a purity level of at least about 97%; and
   (b) water, present in a maximum amount of about 10 wt. %, based on the weight of the composition.

2. The composition of claim 1 wherein the purity level is at least 99%.

3. The composition of claim 1 wherein water is present in a maximum amount of 5 wt. %, based on the weight of the composition.

4. The composition of claim 3 wherein the water is present in a maximum amount of 3 wt. %, based on the weight of the composition.

5. The composition of claim 1 wherein the metal comprises sodium.

6. The composition of claim 1 wherein the metal comprises manganese.

7. A process for preparing a composition comprising the compound glucosamine sulfate metal chloride, wherein the metal is selected from the group consisting of lithium, sodium, magnesium, zinc and manganese, said compound having a purity level of at least about 97%, which comprises the steps of:
   (a) contacting glucosamine hydrochloride with a sulfate of said metal in the presence of water to form an aqueous solution of glucosamine sulfate metal chloride; and
   (b) recovering the compound by freeze-drying the solution from step (a) at a temperature and at a reduced pressure for such period of time that: (i) at least about 90 wt. % of the water is removed and (ii) decomposition of the compound glucosamine sulfate metal chloride is limited to a maximum of about 3%.

8. The process of claim 7 wherein the glucosamine hydrochloride and metal sulfate are contacted in stoichiometric quantities in the presence of sufficient water to form a concentration of solids of about 15 to 40 wt. %, and the contacting in step (a) takes place for a period of about 15 minutes to 2 hours.

9. The process of claim 7 wherein the water is present in step (a) in an amount such that the concentration of solids is in the range of 20 to 30 wt. %, based on the weight of water plus solids.

10. The process of claim 7 wherein step (a) takes place at a temperature in the range of about 20 to 45° C.

11. The process of claim 7 wherein the freeze-drying is carried out at a pressure of not greater than about 800 milliTorr and at a temperature in the range of about −60° C. to 0° C.

12. The process of claim 11 wherein the freeze-drying is carried out at a pressure in the range of 300 to 500 milliTorr and a temperature in the range of −40 to −5° C.

13. The process of claim 7 wherein the metal sulfate comprises sodium sulfate.

14. The process of claim 7 wherein the metal sulfate comprises manganese sulfate.

* * * * *